United States Patent [19]

Riewenherm

[11] Patent Number: 5,490,780
[45] Date of Patent: Feb. 13, 1996

[54] DENTAL SUCTION CANNULA

[76] Inventor: Ulrich Riewenherm, Isselhorster Str. 234, D-33335 Gütersloh, Germany

[21] Appl. No.: 219,345

[22] Filed: Mar. 29, 1994

[30] Foreign Application Priority Data

Mar. 30, 1993 [DE] Germany .......................... 43 10 225.5

[51] Int. Cl.$^6$ ................................................ A61C 17/06
[52] U.S. Cl. ..................................... 433/93; 433/31
[58] Field of Search ........................... 433/31, 91, 93, 433/94, 136

[56] References Cited

U.S. PATENT DOCUMENTS

| | | | |
|---|---|---|---|
| 692,281 | 2/1902 | Hare | 433/93 |
| 2,574,217 | 11/1951 | Lundren et al. | 433/31 |
| 3,772,790 | 11/1973 | Swan-Gett et al. | 433/136 |
| 5,037,298 | 8/1991 | Hickham | 433/93 |

FOREIGN PATENT DOCUMENTS

| | | | |
|---|---|---|---|
| 2677538 | 12/1992 | France | 433/94 |
| 242045 | 9/1946 | Switzerland | 433/94 |

*Primary Examiner*—Cary E. O'Connor
*Attorney, Agent, or Firm*—Burns, Doane, Swecker & Mathis

[57] ABSTRACT

A dental suction cannula comprises a suction conduit which carries a protection head. The protection head is U-shaped and forms a space for receiving the tooth ridge of the patient's mouth. A suction opening of the conduit communicates with that space to suction moisture therefrom. Inner surfaces of the protection head have a mirror finish to reflect light.

19 Claims, 2 Drawing Sheets

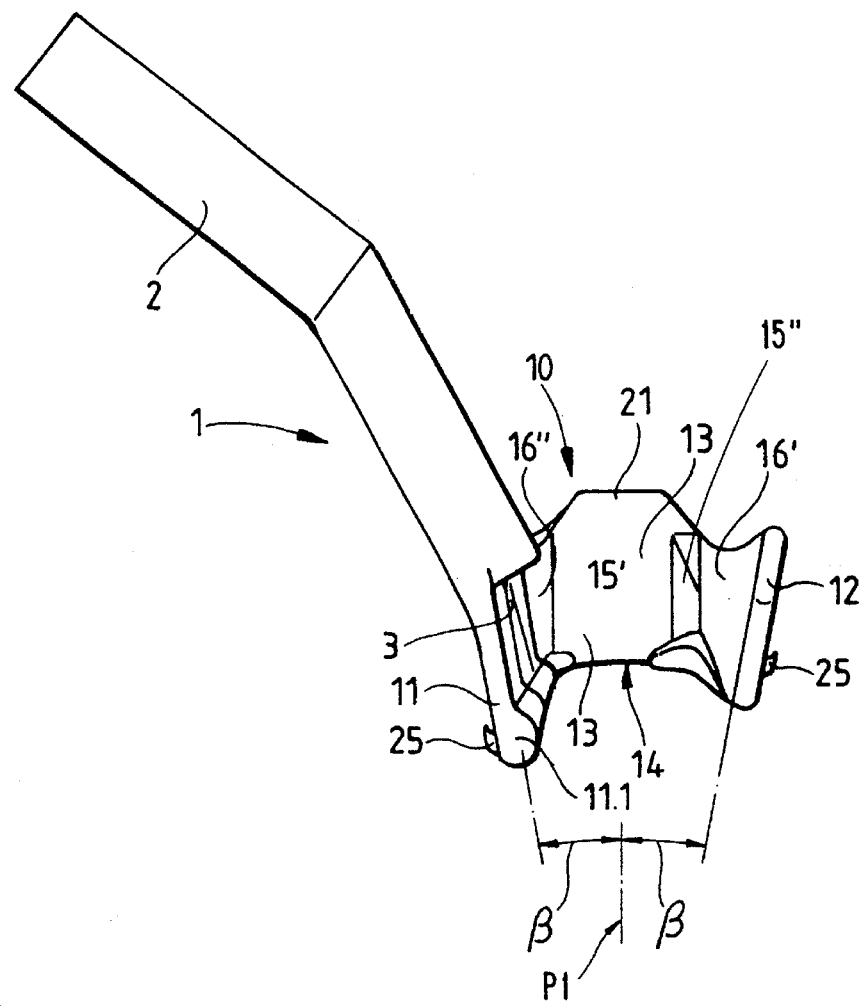
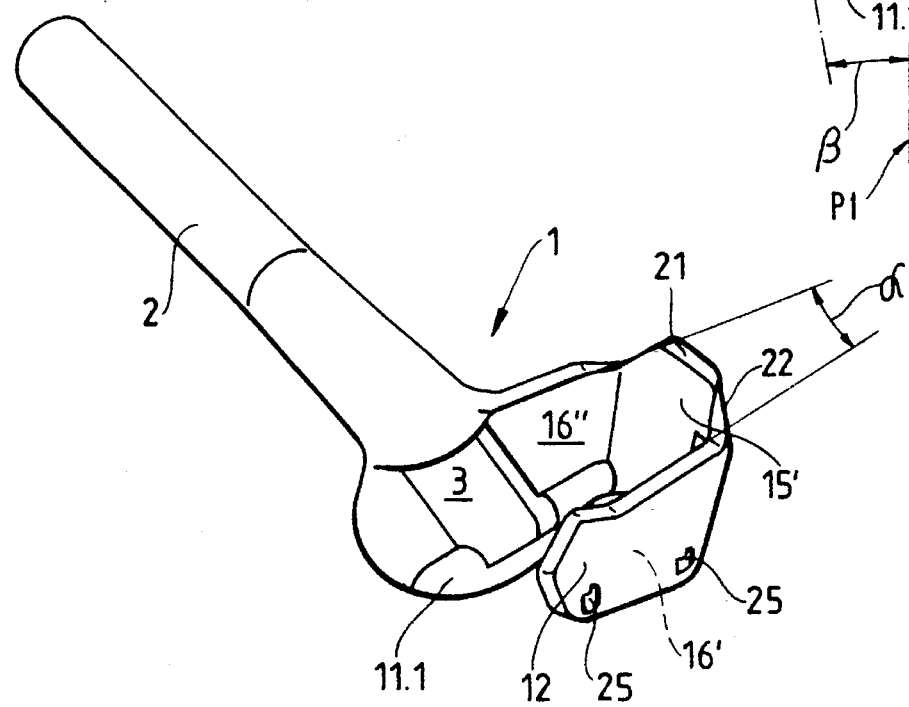

1

DENTAL SUCTION CANNULA

BACKGROUND OF THE INVENTION

The invention relates to a suction cannula for dental purposes.

In the dental office, preparations have to be conducted in the mouth region, thus working with high speed instruments. The dental sites that are processed with these instruments must be cooled, to which end the drill or turbine heads are provided with water jets focused on the region to be treated. To properly see the mouth region the dentist requires illumination; to have adequate illumination, the light beam of the treatment lamp is directed into the mouth cavity, whereby it is important that the mouth is opened wide in order to achieve the desired illumination. To improve this illumination, the dentist uses a mouth mirror, with which the progress of the work can be monitored. With this mouth mirror the dentist can also protect either the tongue or the inside of the cheek from injury caused by the working device that is used. As a rule an assistant, who holds a suction cannula at the region to be treated in order to siphon off the sprayed water, assists with this work. With this suction cannula the inside of the cheek or the tongue, which cannot be protected from the mouth mirror of the dentist, is protected in that the suction cannula, which acts simultaneously as a protective umbrella, pushes back that part of the cheek that faces the region to be treated and that part of the tongue that faces the region to be treated and, thus, rules out the risk generated by the working instruments of the dentist.

However, as an assisting helper is not available in all cases the dentist may have to manage without this assistance. As a result, the patient is, first of all, endangered, and secondly the dentist is forced to change instruments, a procedure that requires manipulations that disturb the treatment sequence.

An object of the invention is to improve the existing suction cannulas in such a manner that the aforementioned drawbacks are avoided and the dentist can also treat a patient without assistance and without endangering said patient due to the working instruments and at the same time is released from unnecessary manipulations in order to change instruments. In addition, this improvement shall be simple to use, reliable, and economical to produce.

SUMMARY OF THE PREFERRED EMBODIMENTS OF THE INVENTION

This problem is now solved according to the invention by means of a U-shaped protection head which exhibits two side walls and an apex section connecting these side walls, whereby the suction opening of the cannula opens into the first of the side walls of the "U"; and the second side wall of the "U", opposite the side wall with the suction opening, is offset vertically with respect to this first side wall; and the apex section of the "U" is shaped in such a manner that it extends over the dental tooth ridge. This design provides a suction cannula that is adapted to the operating mode of the dentist; he can hold said suction cannula so gently that the soft parts in the vicinity of the region to be treated—the cheek, on the one hand, and the tongue, on the other hand—are especially protected. At the same time he/she can hold the mouth piece with the other hand and guide it in such a manner for preparation that he/she can conduct his work undisturbed.

In an advantageous embodiment, the protection head is molded as one piece to the suction conduit of the cannula. As an alternative, the protection head is designed as a metal or an injection molded plastic article having a connection sleeve that can be attached to the suction opening of the suction conduit. Snap-in elements, for example snap-in segments or snap-in pins in interaction with corresponding snap-in grooves or snap-in notches, can connect the sleeve to the suction conduit. Whereas the first of the two embodiments is designated as a "disposable cannula" in the second embodiment the protection head can be replaced, so that here conventional stainless steel protection heads can be employed, in which is received the dental ridge with the "U" reaching over the tooth or teeth, and can be replaced from patient to patient.

For the design as a plastic article, a hygienically safe and sterilizable plastic is provided that also allows, if injection moldable, the protection head can be produced by an injection molding process. This applies to the case where the protection head and the suction conduit are integral, as well as to the case where the protection head is an attachment. The dentist can introduce this suction cannula, designed thus, into the mouth cavity, whereby the protection head lies on both sides of the tooth to be treated, and the apex section extends over the dental ridge. In this manner the region to be treated is defined. Owing to the shape of the protection head the two side walls lie in essence parallel to the dental ridge, thus enabling work in all four quadrants of the jaw. The two side walls protect the soft parts adjacent to the region to be treated from harm caused by the treatment tools; at the same time the play of the tongue, which is pleasant for the patient, remains unaffected so that swallowing movements are possible. Both the respective edges of the side walls facing the occlusion and the edges of the apex section facing the dental ridge can be braced individually or jointly against the bottom of the jaw or gum. Thus, the dentist has the option of finding a support point for the hand guiding the treatment tool, a feature that significantly improves the accuracy of the guide of the treatment tool as compared to a free-hand guide. Secondly, by demarcating the region to be treated the air flow in the region to be treated is significantly increased, a feature that raises the efficiency of the suction operation. At the same time the suction opening in the side wall attached to the cannula is arranged in such a manner that its center lies on a level of the equator of the tooth to be treated. It is obvious that different configurations of the suction cannula are also possible, if necessary, for the individual quadrants or for right or left handedness of the treating dentist, while maintaining the basic U-shape.

In a preferred embodiment the protection head exhibits a mirror surface, focused on the interior of the open "U" of the protection head, at least in the region of the apex section. First, light is "caught" by means of this mirror surface on the apex section and optionally on one or both side faces and reflected on the region to be treated; secondly, the dentist has the customary observation possibility, without needing an additional mouth mirror, since the suction cannula that is designed in this manner can be guided like a mouth mirror. In an advantageous embodiment the finish of the mirror surface is formed by mirror-coated surfaces, which are provided on the inner surfaces of at least one of the side walls and/or the apex section and which can be applied by means of vaporization or electroplating. It is advantageous if these mirror surfaces are applied by means of the plasma ion coating process. To this end, ions, which impinge on the surfaces to be metallized and precipitate there, are produced with means of discharge in gas. It is advantageous to apply first a copper substrate, on which then the reflecting layer is applied, for example a titanium or chromium layer. It is self-evident that the metallized inner surfaces are designed sufficiently flat, a feature that can be achieved by a production process adapted to this condition.

First, with this arrangement of the mirror or mirrors the light coming in from the treatment lamp is focused on the area to be treated, so that the desired illumination is guaranteed, whereby it is self-evident that the illumination depends on the place to be prepared at the tooth; secondly, the dentist is given the possibility of inspecting the area to be treated, so that he can detect the residual defects, in particular the residual caries. At the same time the dentist, who holds freely the suction cannula provided with the protection head, can adjust the mirror in such a manner that the illumination of the region to be treated is optimal for him. it is obvious that this illumination and the observation possibilities can also be obtained by providing a conventional mirror in the region of the apex section and/or the side walls.

It is advantageous to design the protection head as U-shaped whereby the angle a of the two side faces of the "U" ranges up to 40°. With this opening the dentist also has adequate space for preparing the side areas of the tooth.

To obtain improved access to the region to be treated, it is advantageous, if at least the second side wall opposite the first side wall provided with the suction opening is outwardly sloped by an angle β of up to about 20°.

In consideration of the different shapes of the lower jaw - buccal cavity and the bottom of the tongue or the upper jaw buccal cavity and the gum, it is also advantageous, if the outer, second side wall opposite the first side wall provided with the suction opening forms in such a manner an angle δ of at most 30° with the longitudinal reach of the first side wall that the free end of the second side wall at least reaches, if not even projects beyond, the upper edge of the first side wall.

At the same time it is advantageous if the apex section and/or the second side wall of the protection head exhibits a width that is shorter with respect to the first side wall with the suction opening. This embodiment takes into consideration that the side face of the protection head that faces the cheek can reach deeper into the buccal cavity than the side face facing the tongue. When the region of the premolar is being treated, the apex section can be guided effortlessly over a tooth lying behind the tooth to be treated, whereby the apex section can even be braced against this tooth. When the region of the furthest posterior molar is being treated, the apex section reaches over the dental ridge.

It is also advantageous to design the bottom edge of at least the side wall with the suction opening as a doughnut and to bend it over preferably in the direction of the free side wall. This doughnut rests in the depth of the buccal cavity against its base or against the dental ridge, thus resulting in a closure that delimits the region of treatment. To make a treatment more tolerable for the patient, it is also advantageous, if the upper edge of the apex section exhibits a bite ridge. The patient can "bite down" on this bite ridge and thus relieve the musculature. Furthermore, in an advantageous embodiment the upper edge of the apex section of the protective shoulder exhibits a bite ridge.

With the suction cannula created in such a manner the dentist is furnished with an instrument that offers him/her the possibility of also doing different preparations without an assistant, whereby the attachment can be braced against the tongue bottom or against the gum and, thus, a fixed point is created that can serve the dentist to brace the hand guiding the handpiece. During said procedure the patient also perceives relief, because the assistant's hand that always moved in his field of vision drops out, and because the protection of the soft parts is improved without significantly restricting the mobility of the tongue and because the very effective suction deals with a greater amount of water used for cooling, so that less water can collect in the deeper situated parts of the mouth cavity, which can give fewer reasons for swallowing, on the one hand, and which can be swallowed without further ado owing to the preserved mobility of the tongue, on the other hand. Finally the protection head can be designed in such a manner that a rubber cofferdam can be attached that wraps itself with ease in a protective manner around the region to be treated and which is held under tension by means of the pressure exerted on the suction cannula. To this end, the side walls of the attachment are provided in a simple manner with cams, from which the rubber cofferdams can be suspended and held under tension.

BRIEF DESCRIPTION OF THE DRAWINGS

The objects and advantages of the invention will become apparent from the following detailed description of the preferred embodiments thereof in connection with the accompanying drawing in which like numerals designate like elements and in which:

FIG. 4 is a front view of the suction cannula shown in FIG. 1, with the addition of side mirrors and protuberances for attaching a rubber cofferdam; and FIG. 5 is a top perspective view of the suction cannula shown in FIG. 4.

DETAILED DESCRIPTION OF PREFERRED EMBODIMENTS OF THE INVENTION

Figure 1:
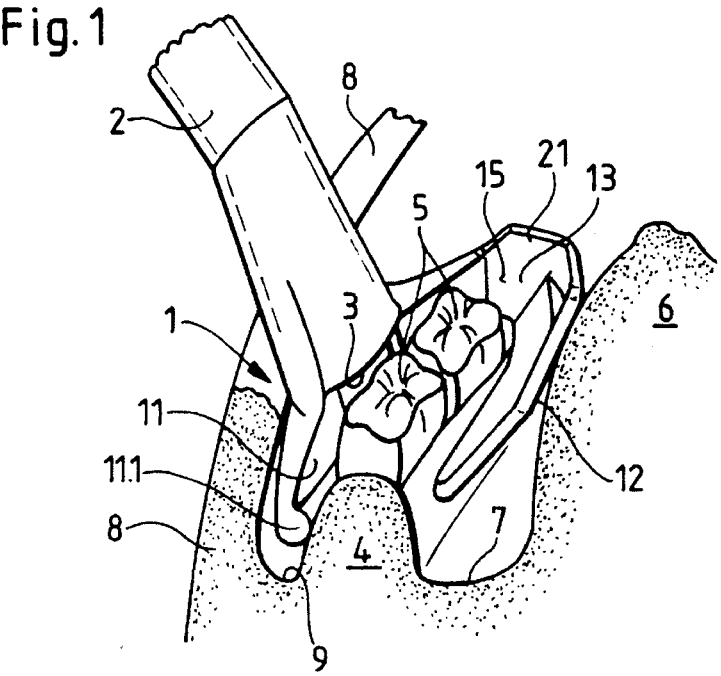
FIG. 1 is a perspective view of the suction end of a suction cannula with attachment disposed in a mouth region to be treated.

FIG. 1 is a perspective view of an embodiment of the suction cannula 1 for dental purposes, where the suction end of a suction conduit 2 carries a protection head 10 that is inserted into the IV quadrant of the lower jaw and extends across the dental ridge 4 having teeth 5. The suction end of the suction conduit 2, which adjoins the side wall 11 of the protection head, has a suction opening 3. Side walls 11 and 12 of the protection head 10 lie adjacent respective sides of the dental ridge 4 so that the teeth 5 lie between the two side walls 11 and 12 of the protection body 10, whereby said protection body is braced against the bottom 7 of tongue 6 and/or against the bottom 9 of the buccal cavity 8 (whereby it is obvious that the analogous situations are possible in the other quadrants of the mouth).

Figure 2:
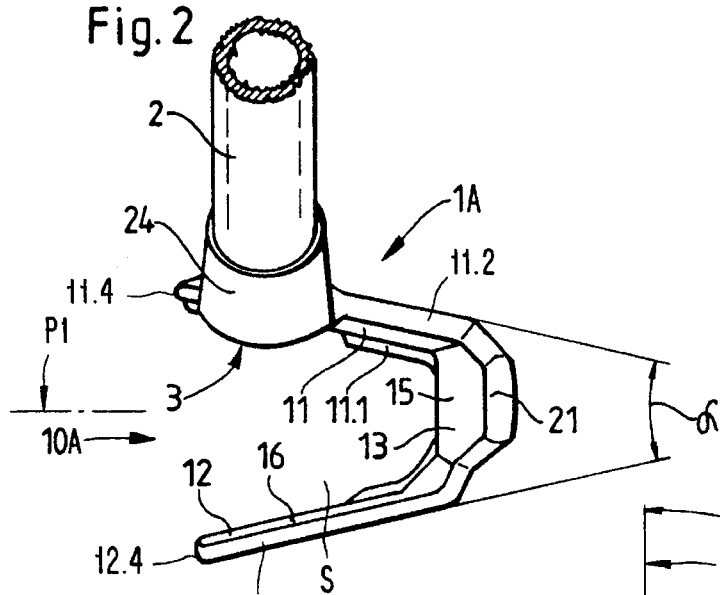
FIG. 2 is a top view of the suction cannula corresponding to that of FIG. 1, except that the manner of mounting a protection head thereof is slightly modified.

In FIGS. 1 and 3–5, the protection head 10 is integrally molded with the cannula 1, whereas in FIG. 2 the protection head 10A is formed separately of the cannula 1A and is attached thereto.

The suction cannula 1 is designed in the conventional manner; it includes a hose connection (not illustrated in detail here); and forms the suction end 2 with the suction opening 3. The protection body 10, which is molded with the suction cannula 1 (or connected as an attachment in the embodiment according to FIG. 2) has in essence a "U" shape and is provided with the first side wall 11, disposed below the suction opening 3, and an opposing second side wall 12, which walls are connected together by means of an apex section 13. The height H of the interconnection of the side walls 11, 12 with the apex section 13 is slightly less than the height H' of the apex portion. The free ends 11.4, 12.4 of the walls 11, 12 define the opening of a space S defined by the "U". In the embodiment according to FIGS. 1 and 3–5, the head 10 is molded of one piece with the suction cannula 1, preferably by injection molding. The embodiment of the head 10A shown in FIG. 2 is produced as a separate part and is provided with a socket 24, into which the suction end 2 of the suction cannula 1 can be inserted. Any suitable locking can be provided such as friction-fit, adhesive fasteners, snap-in elements, etc., that fix together the suction cannula 1A and head attachment 10A.

The first and second side walls 11, 12 are spaced from opposite sides of a first reference plane P1 (see FIG. 2) which bisects the space S formed by the wall arrangement 11, 12, 13. The first side wall 11 includes first and second edges 11.2, 11.3 disposed on opposite sides of a second reference plane P2 (FIG. 3) oriented perpendicular to the first reference plane P1. The second side wall 12 includes first and second edges 12.2, 12.3 disposed on opposite sides of the second reference plane P2. The apex portion 13 includes first and second edges 13.2, 13.3 disposed on opposite sides of the second reference plane P2. The axis of the suction opening 3 lies in a third reference plane P3 (FIG. 3) which is oriented perpendicular to both of the first and second reference planes P1, P2. The height of the space S is defined by a dimension thereof oriented in the first reference plane P1 and extending perpendicular to the second reference plane P2. That height is at least as great as the conventional height of a tooth ridge 4.

Each of the side walls 11, 12 includes a width W. The width W of the side wall 12 is designated in FIG. 3; that width is shorter than the width of the side wall 11.

Each of the widths of the side walls 11 and 12 is at least as large as the conventional height of the toothed dental ridge 4 of the jaw, so that both side walls 11 and 12 in the treatment or operative position extend at least up to the upper edges of the teeth 5 situated in the dental ridge 4; the two side walls 11 and 12 come to rest on opposite sides of the dental ridge 4. To maintain this position, the apex section 13 of the attachment 10 can be provided with a notch 14, so that this apex can extend without any difficulties over the dental ridge 4 (and optionally also over a tooth 5 located therein). The depth of the notch 14 would be adapted to the customary heights of the teeth. To avoid excess pressure in the region of the contact points (especially in the case of metal attachments 10A), the bottom rim regions are provided advantageously with a bulge, e.g., see bulge or bead 11.1, which is obtained during molding (or in the case of metal attachments 10 also by beading).

The plane P3, and thus the axis of the suction opening 3, forms an angle e with the second reference plane P2 as viewed in a direction perpendicular to the first reference plane P1 (FIG. 3), the angle $\epsilon$ ranging from 80° to 135°. The suction cannula can be inserted into the mouth of the patient in such a manner that to prepare a tooth both side walls 11 and 12 of the head 10, 10A lie next to the dental ridge 4 of the jaw quadrant, in which the tooth 5 to be prepared is located, whereby any jaw quadrant can be reached. With this design the preparation region is further defined; nevertheless, the dentist can insert a handpiece into the site to be prepared without any impediment, whereby the region to be prepared is further defined by the head of the handpiece. At the same time the dentist holds the suction cannula 1 with the one hand and the handpiece with the treatment tool with the other hand and thus both this handpiece and the suction cannula can be arranged in accordance with the local peculiarities of the region to be treated in one of the four quadrants.

To illuminate the region to be treated, the inner surface of the apex section 13 is provided with a mirror surface 15, which is designed as a metallized surface. The same also applies to the side wall 12, which lies opposite the side wall 11 provided with the suction opening 3, whereby here the mirror 16 is at right angles to the mirror 15 of the apex section 13. The mirror 15 of the apex section 13 has an outwardly oriented angle (angle $\delta$, FIG. 3) up to 20° with respect to the attachment 10, so that incident light is well reflected into the region to be treated. That is, the apex portion 13 is inclined at an oblique angle $\delta$ with respect to the second reference plane P2 such that the first edge 13.2 thereof is spaced farther from the third reference plane P3 than the second edge 13.3 thereof.

Correspondingly the mirror 16, provided in the side wall 12 has an outwardly directed slope of up to 20° (angle $\beta$, FIG. 4). That is, the second side wall 12 is inclined at an oblique angle $\beta$ with respect to the first reference plane P1 such that the first edge 12.2 of the second side wall is spaced farther from the first reference plane P1 than the second edge 12.3 thereof. Likewise, the first side wall 11 forms a similar angle $\beta$ of no more than 20° with respect to the first reference plane P1.

Figure 3:
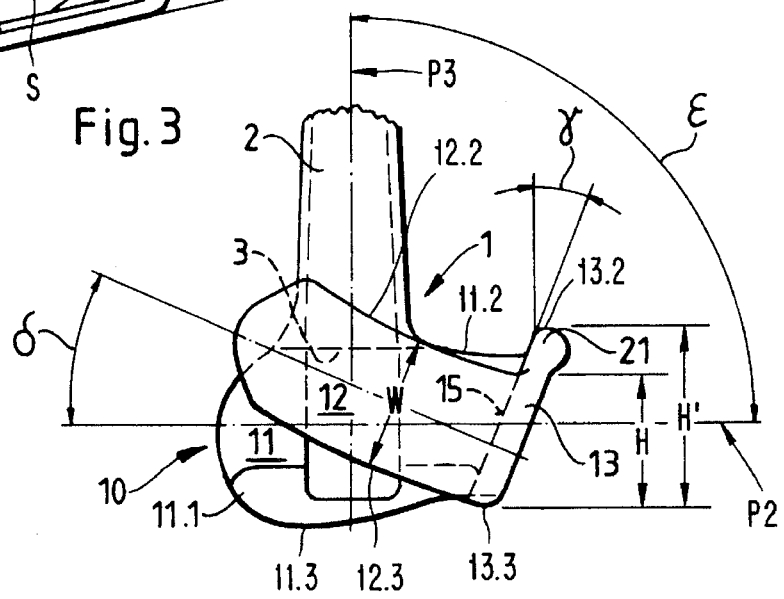
FIG. 3 is a side view of the suction cannula shown in FIG. 1.

FIG. 4 shows the opening of the "U", whose angle $\alpha$ (FIG. 2) ranges up to 40° in everyday practice. That is, the side walls 11, 12 diverge toward their free ends at an angle $\alpha$ of up to 40°. The second side wall 12 extends from the apex portion 13 at an angle $\delta$ of no more than 30° with respect to the second reference plane P2 (FIG. 3) such that the free end 12.4 of the second side wall extends at least to, and preferably beyond, the height of the first edge 11.2 of the first side wall 11, as viewed in a direction perpendicular to the first reference plane P1 (FIG. 3).

In the embodiment according to FIG. 4, the insides of the side walls are also metallized, thus resulting in the mirrors 15' and 16' and 16", whereby it is evident that these surfaces exhibit the requisite flatness owing to production. To avoid optical distortions, the angular or rounded off transitions are excluded from the metallization. If the inside of the apex section 13 is designed "bent", the result is another mirror 15", so that there are in total 4 mirrors, which, first of all, direct the light into the region to be treated, but which secondly allow the dentist an overview over the region to be treated with its surrounds, to recognize residual defects, like residual carries. An overall metallization is advantageous, whereby the regions of the inside and outside surfaces, which are not to reflect, are made matted or non-polished. This overall metallic coating is advantageous with respect to hygienic considerations; it coats the attachment without gaps and, thus, allows flawless sterilization.

The rear surface of the apex section 13 is shaped in such a manner that a bite bulge 21 has adequate space to enable the patient to bite down on this bite bulge to relax the muscles. The bite bulge is interconnected with the side walls 11, 12 by inclined edges 22 (see FIG. 5). The outside of the side walls (in FIG. 5 only the second side wall 12 is visible) have suspension protuberances 25 for the attachment of a rubber cofferdam. The situation of these suspension protuberances is such that the dental ridge with the teeth clamps the rubber cofferdam at the protection head put into the mouth and, thus, represents an advantageous holding device.

Although the invention has been described in connection with preferred embodiments thereof, it will be appreciated by those skilled in the art that additions, modifications, substitutions, and deletions not specifically described may be made without departing from the spirit and scope of the invention as defined in the appended claims.

What is claimed is:

1. A dental suction cannula, comprising a suction conduit having a suction opening; a protection head connected to an end of said suction conduit for being placed in a patient's mouth; said protection head including a wall structure comprised of a pair of side walls having interconnected ends interconnected by an apex portion of said wall structure; said side walls including spaced-apart free ends such that said wall structure is U-shaped; said side walls being spaced apart to define therebetween a space in which a toothed ridge of a patient's mouth can be received, with said side walls disposed on opposite sides of the toothed ridge, and said apex portion extending across the toothed ridge; said suction opening communicating with said space for suctioning moisture therefrom, a height of said apex portion being at least as great as a height of said interconnected ends of said side walls.

2. A dental suction cannula according to claim 1, wherein said side walls are of one piece with one another and with said suction conduit.

3. A dental suction cannula according to claim 2, wherein said wall structure forms an inner surface arrangement facing said space, at least a portion of said inner surface arrangement has a light-reflecting mirror finish.

4. A dental suction cannula according to claim 3, wherein said portion of said inner surface arrangement is disposed on said apex portion.

5. A dental suction cannula according to claim 3, wherein said portion of said inner surface arrangement is disposed on at least a first of said side walls.

6. A dental suction cannula according to claim 5, wherein said side walls are spaced from opposite sides of a first imaginary reference plane which bisects said space, each of said side walls and said apex portion including first and second edges lying on opposite sides of a second reference plane oriented perpendicular to said first reference plane, said suction opening situated adjacent said first edge of a first of said side walls, said first side wall being inclined to form an oblique angle with respect to said first reference plane such that said first edge thereof is spaced farther from said first reference plane than said second edge thereof.

7. A dental suction cannula according to claim 6, wherein said oblique angle is no greater than about 20 degrees.

8. A dental suction cannula according to claim 6, wherein said first side wall is inclined to form an oblique angle with respect to said first reference plane such that said first edge thereof is spaced farther from said first reference plane than said second edge thereof.

9. A dental suction cannula according to claim 3, wherein said portion of said inner surface arrangement is metallized to form said mirror finish.

10. A dental suction cannula according to claim 1, wherein said side walls are spaced from opposite sides of a first imaginary reference plane which bisects said space, and each of said side walls including first and second edges disposed on opposite sides of a second reference plane oriented perpendicular to said first reference plane, said suction opening being situated adjacent said first edge of one of said side walls, the other side wall extending from said apex portion at an acute angle of no more than about 30 degrees with reference to said second reference plane and with reference to said one side wall, such that said free end of said other side wall extends at least to the height of said first edge of said one side wall as viewed in a direction perpendicular to said first reference plane.

11. A dental suction cannula according to claim 1, wherein said side walls are spaced from opposite sides of a first imaginary reference plane which bisects said space, and an axis of said suction conduit intersecting a second imaginary reference plane oriented perpendicular to said first reference plane to form with said second reference plane an angle in the range of 80–135 degrees as viewed in a direction perpendicular to said first reference plane.

12. A dental suction cannula according to claim 1, wherein said side walls are spaced from opposite sides of a first imaginary reference plane which bisects said space, a height of said space being defined by a dimension of said space lying in said first reference plane and extending perpendicular to a second imaginary reference plane oriented perpendicular to said first reference plane, said height being at least as great as that of a tooth ridge of a patient's mouth.

13. A dental suction cannula according to claim 1, wherein said suction conduit is connected to one of said side walls and extends upwardly therefrom in a general direction of a height of said one side wall.

14. A dental suction cannula according to claim 1, wherein said apex portion includes a notch formed in a mid-region of a lower edge thereof.

15. A dental suction cannula, comprising a suction conduit having a suction opening; a protection head connected to an end of said suction conduit for being placed in a patient's mouth; said protection head including a wall structure comprised of a pair of side walls having interconnected ends interconnected by an apex portion of said wall structure; said side walls being spaced apart to define therebetween a space in which a toothed ridge of a patient's mouth can be received, with said side walls disposed on opposite sides of the toothed ridge, and said apex portion extending across the toothed ridge; said suction opening communicating with said space for suctioning moisture therefrom; wherein said side walls are spaced from opposite sides of a first imaginary reference plane which bisects said space; each of said side walls including first and second edges lying on opposite sides of a second reference plane oriented perpendicular to said first reference plane; said suction opening being situated adjacent said first edge of a first of said side walls; a height of said space being defined by a dimension of said space lying in said first reference plane and extending perpendicular to said second imaginary reference plane; said first edge of a second of said side walls extending higher than said first edge of said first side wall.

16. A dental suction cannula, comprising a suction conduit having a suction opening; a protection head connected to an end of said suction conduit for being placed in a patient's mouth; said protection head including a wall structure comprised of a pair of side walls having interconnected ends interconnected by an apex portion of said wall structure; said side walls being spaced apart to define therebetween a space in which a toothed ridge of a patient's mouth can be received, with said side walls disposed on opposite sides of the toothed ridge, and said apex portion extending across the toothed ridge; said suction opening communicating with said space for suctioning moisture therefrom; wherein said wall structure forms an inner surface arrangement facing said space; at least a portion of said inner surface arrangement has a light-reflecting mirror finish and is disposed on said apex portion; said side walls being spaced from opposite sides of a first imaginary reference plane which bisects said space; each of said side walls and said apex portion including first and second edges lying on opposite sides of a second reference plane oriented perpendicular to said first reference plane; said suction opening being intersected by a third reference plane oriented perpendicular to each of said first and second reference planes, said suction opening situated adjacent said first edge of a first of said side walls; said apex portion being inclined to form an oblique angle with respect to said third reference plane such that said first edge of said apex portion is situated farther from said third reference plane than said second edge thereof.

17. A dental suction cannula according to claim 16, wherein said oblique angle is no greater than about 20 degrees.

18. A dental suction cannula, comprising a suction conduit having a suction opening; a protection head connected to an end of said suction conduit for being placed in a patient's mouth; said protection head including a wall structure comprised of a pair of side walls having interconnected ends interconnected by an apex portion of said wall structure; said side walls being spaced apart to define therebetween a space in which a toothed ridge of a patient's mouth can be received, with said side walls disposed on opposite sides of the toothed ridge, and said apex portion extending across the toothed ridge; said suction opening communicating with said space for suctioning moisture therefrom; wherein said side walls are spaced from opposite sides of a first reference plane which bisects said space; each of said side walls including first and second edges disposed on opposite sides of a second reference plane oriented perpendicular to said first reference plane; said suction opening disposed adjacent said first edge of a first of said side walls; a second of said side walls being inclined at an oblique angle of no more than about 20 degrees with respect to said first reference plane such that said first edge of said second side wall is spaced farther from said first reference plane than said second edge thereof.

19. A dental suction cannula according to claim 18, wherein said side walls are spaced from opposite sides of a first imaginary reference plane which bisects said space, each of said side walls including first and second edges lying on opposite sides of a second reference plane oriented perpendicular to said first reference plane, said suction opening situated adjacent said first edge of a first of said side walls, said first edge of said first side wall being shaped as a bead projecting toward said second side wall.

* * * * *